United States Patent [19]

Töpfl et al.

[11] Patent Number: 5,133,779
[45] Date of Patent: Jul. 28, 1992

[54] CATIONIC REACTION PRODUCTS OF BASIC CARBAMIDES AND EPIHALOHYDRINS: QUATERNARY AMMONIUM SALTS AS DYEING AIDS FOR CELLULOSE

[75] Inventors: Rosemarie Töpfl, Dornach; Jörg Binz, Reinach, both of Switzerland

[73] Assignee: Ciba-Geigy Corporation, Ardsley, N.Y.

[21] Appl. No.: 771,087

[22] Filed: Oct. 2, 1991

Related U.S. Application Data

[60] Division of Ser. No. 327,354, Mar. 21, 1989, Pat. No. 5,081,294, which is a continuation of Ser. No. 75,804, Jul. 20, 1987, abandoned.

[30] Foreign Application Priority Data

Jul. 31, 1986 [CH] Switzerland .................. 3082/86-2

[51] Int. Cl.$^5$ .............. C09B 67/00; C07C 275/14; C07D 233/61; D06P 1/66
[52] U.S. Cl. ............................. 8/606; 8/543; 8/680; 8/918; 564/59
[58] Field of Search .............................. 8/606

[56] References Cited

U.S. PATENT DOCUMENTS

| | | | |
|---|---|---|---|
| 4,424,284 | 1/1984 | Haase et al. | 521/36 |
| 4,478,724 | 10/1984 | Haase et al. | 210/679 |
| 4,506,081 | 3/1985 | Fenyes et al. | 548/523 |
| 4,581,058 | 4/1986 | Fenyes et al. | 544/357 |
| 4,851,139 | 7/1989 | Lems et al. | 252/8.8 |
| 4,970,066 | 11/1990 | Grollier et al. | 8/406 |
| 5,081,294 | 1/1992 | Topfl et al. | 564/59 |

Primary Examiner—A. Lionel Clingman
Attorney, Agent, or Firm—Marla J. Mathias; Edward McC. Roberts

[57] ABSTRACT

There are disclosed quaternary ammonium salts which are obtainable by reacting basic carbamides containing a quaternizable nitrogen atom with epihalohydrins.

These quaternary ammonium salts are particularly suitable for enhancing the color yield and the wet fastness properties of dyeings or printings produced on cellulosic fibre materials with anionic dye, e.g. reactive or direct dyes.

5 Claims, No Drawings

CATIONIC REACTION PRODUCTS OF BASIC CARBAMIDES AND EPIHALOHYDRINS: QUATERNARY AMMONIUM SALTS AS DYEING AIDS FOR CELLULOSE

This is a divisional of Ser. No. 327,354, filed Mar. 21, 1989, now U.S. Pat. No. 5,081,294, issued Jan. 14, 1992, which in turn is a continuation of Ser. No. 075,804, filed Jul. 20, 1987, now abandoned.

Direct dyes cannot be applied to cellulose fibres by the pad-batch process or application is only possible with insufficient colour yield. When dark shades are required, these fibres must therefore be dyed by an exhaust method. This method is very expensive, as it gives rise to increased energy and chemical costs. Moreover, as regards the fastness standard, dyeings of this type do not satisfy all requirements. Despite aftertreatment with conventional cationic aftertreatment agents, such dyeings are not fast to the now usual 60° C. wash in the presence of sodium perborate, thereby severely limiting the scope for their use, especially in the clothing sector.

It was hoped that the use of reactive dyes had solved the problem of water-fastness and above all of wash-fastness, because these dyes form a chemical bond with the cellulose. The dye/fibre bond has, however, been found to be insufficiently stable to acid hydrolysis, and this is again expressed in impairment of the wetfastness properties and particularly of wash-fastness. The no longer chemically fixed dye is dissolved in the washbath and can therefore stain, for example, other textiles simultaneously washed in the same washing operation. A further disadvantage of dyeing with reactive dyes is the high dye loss when washing off the dyeing, as not all the dye applied is chemically bonded to the fibre. Losses of up to 60% washing out, depending on the type of dye. For faultless dyeing it is therefore necessary to employ very expensive washing and rinsing processes to remove the non-fixed dye from the fibres. New cationic improvers have now been found that significantly enhance the wet fastness properties of dyeings obtained on cellulose with direct dyes, and also produce an increase in the colour yield. These products can be applied either in a pretreatment or direct during dyeing of the cellulose material.

Accordingly, the present invention relates to cationic reaction products of basic carbamides and epihalohydrins containing a quaternisable nitrogen atom.

Preferred reaction products are those of formula:

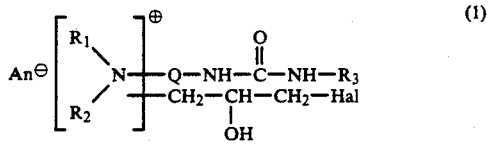

in which
Q is alkylene of 2 to 6 carbon atoms,
$R_1$ and $R_2$ are each independently the other lower alkyl, unsubstituted or substituted by halogen, hydroxyl, cyano or lower alkoxy or cycloalkyl or aralkyl, or
$R_1$ and $R_2$ together with the nitrogen atom to which they are attached are a five- or six-membered heterocyclic radical which may contain an additional heteroatom,
$R_3$ is hydrogen, lower alkyl or hydroxy-lower alkyl,
Hal is a halogen atom, and
$An^\ominus$ is the anion of an organic or inorganic acid, and the halohydrin group is bound to a quaternary nitrogen atom.

Halogen signifies, for example, fluorine, bromine, iodine or, preferably, chlorine. Lower alkyl and lower alkoxy normally represent groups or moieties which contain 1 to 5, especially 1 to 3, carbon atoms. Lower alkyl is e.g. methyl, ethyl, n-propyl, isopropyl, n-butyl, secondary butyl, tertiary butyl, amyl, isoamyl, and lower alkoxy is e.g. methoxy, ethoxy, isopropoxy, tertiary butoxy or tertiary amyloxy.

The alkyl group Q, may, for example, be the

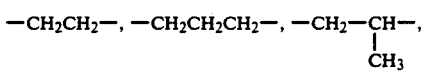

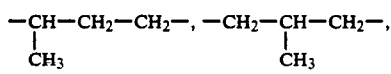

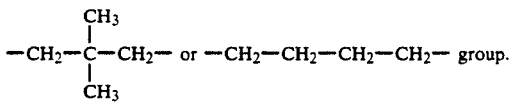

Preferably, Q is the ethylene, 2,2-dimethylpropylene or, most preferably, propylene group $-CH_2CH_2CH_2-$.

The alkyl groups $R_1$ and $R_2$ may be straight-chain or branched. Examples of such groups are methyl, ethyl, n-propyl, isopropyl, n-butyl, secondary butyl, tertiary butyl, n-amyl, isoamyl, or tertiary amyl.

Substituted alkyl groups $R_1$ and $R_2$ are preferably cyanoalkyl, haloalkyl, hydroxyalkyl or alkoxyalkyl groups, preferably of 2 to 6 carbon atoms, e.g. β-cyanoethyl, β-hydroxyethyl, γ-hydroxypropyl, β-methoxyethyl or β-ethoxyethyl. Hydroxymethyl is particularly preferred as the hydroxyalkyl group $R_3$.

Examples of cycloalkyl groups $R_1$ and $R_2$ are cyclopentyl or preferably cyclohexyl. The cycloalkyl groups can contain one or more $C_1$–$C_4$ alkyl moieties, preferably methyl groups. They preferably contain a total of 5 to 10 carbon atoms. A heterocyclic radical $-NR_1R_2$ may be derived from an unsaturated or saturated five- or six-member heterocyclic nitrogen ring, which may contain, in addition to the nitrogen atom, a further heteroatom, such as oxygen, sulfur or also a second nitrogen atom.

$-NR_1R_2$ can thus be, for example, pyrrolidino, piperidino, pipecoline, morpholino, thiomorpholino, piperazino, pyrazolino, pyrazolidinyl or imidazolyl. Piperazino can be substituted by a lower alkyl or benzyl group on the second nitrogen atom.

Particularly preferred heterocyclic radicals $-NR_1R_2$ are pyrrolidino, piperidino, morpholino or imidazolyl.

$R_3$ is preferably hydrogen.
The halohydrin group is preferably

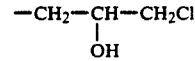

It usually forms the quaternary ammonium group with $-NR_1R_2$. It can however also be bound to a second quaternisable ring nitrogen atom in $-NR_1R_2$.

Suitable anions An$^\ominus$ are anions of inorganic acids, e.g. chloride, bromide, fluoride, iodide, sulfate or phosphate ions, as well as of organic acids, e.g. aromatic or aliphatic sulfonic acids, such as benzenesulfonate, p-toluenesulfonate, chlorobenzenesulfonate, methane- or ethanesulfonate ions, and the anions of lower carboxylic acids, e.g. acetate, propionate or oxalate ions.

An$^\ominus$ is preferably a chloride, bromide or sulfate ion.

Useful cationic compounds are those of formula

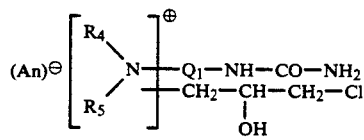
(2)

wherein $R_4$ and $R_5$ are each independently of the other lower alkyl, preferably methyl or ethyl, or —NR$_3$R$_4$ pyrrolidino, piperidino, morpholino or imidazolyl groups, $Q_1$ is ethylene, propylene or 2,2-dimethylpropylene, and An$^\ominus$ has the significance indicated above.

Preferred quaternary ammonium salts of formula (2) are those in which $R_4$ and $R_5$ are identical, and are methyl or ethyl and An$^\ominus$ is a chloride or sulfate ion.

The quaternary ammonium salts are prepared in a manner known per se. Preferably they are prepared by reacting the basic carbamide or its acid salt with, for example, hydrochloric or sulfuric acid, or with an epihalohydrin, such as epibromohydrin, β-methylepichlorohydrin or preferably epichlorohydrin.

The conditions for the quaternisation should be chosen such that no premature exchange of the mobile substituents takes place, as a result of either the pH value of the reaction medium or the temperature being too high. It is therefore preferred to carry out the process in a diluted aqueous medium under carefully monitored temperature and pH conditions, conveniently in the temperature range from 30° to 85° C. and at a pH value from 6 to 8.5, preferably 8. A hydrohalic acid, preferably hydrochloric acid, is used to obtain the desired pH and to obtain the hydrohalide salt.

The basic carbamides required for the quaternisation can be obtained by reacting a corresponding N-substituted diamino compound, e.g. 3-dimethylaminopropylamine, with an urea compound to split off ammonia. The addition salts can be obtained by adding an organic or inorganic acid to the free amines. Basic carbamides of the following formulae have proved to be particularly useful starting materials:

(CH$_3$)$_2$N—CH$_2$CH$_2$CH$_2$—NH—CO—NH$_2$
(CH$_3$)$_2$N—CH$_2$CH$_2$—NH—CO—NH$_2$
(CH$_3$)$_2$N—CH$_2$CH$_2$—NH—CO—NH—CH$_2$OH
(C$_2$H$_5$)$_2$N—CH$_2$CH$_2$—NH—CO—NH$_2$
(C$_2$H$_5$)$_2$N—CH$_2$CH$_2$CH$_2$—NH—CO—NH$_2$ $$\text{(CH}_3\text{)}_2\text{N—CH}_2\text{—}\underset{\underset{\text{CH}_3}{|}}{\overset{\overset{\text{CH}_3}{|}}{\text{C}}}\text{—CH}_2\text{—NH—CO—NH}_2$$

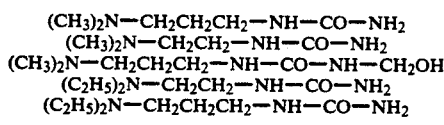

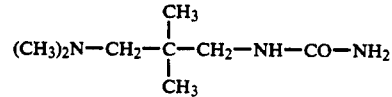

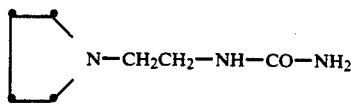

-continued

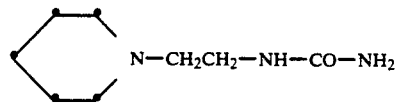

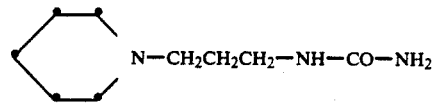

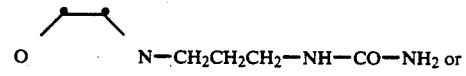

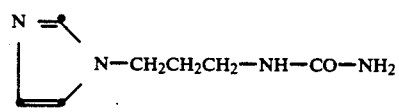

The quaternary ammonium salts of this invention are particularly suitable for improving the colour yield and water-fastness of dyeings or printings obtained on cellulosic fibre materials with anionic dyes, e.g. reactive or direct dyes.

The treatment of the cellulosic material is preferably carried out semicontinuously using the cold-pad batch method. In this method the cellulose material is impregnated with the treatment agent (fixing agent) by printing or preferably by padding, and then subjected to fixing by storage. This application can be made before or during dyeing.

Treatment is preferably made by the cold-pad batch process and especially during the dyeing.

The impregnation can be carried out at 20° to 50° C., but preferably at room temperature. The fixing process is performed by storing the impregnated goods for 4 to 48 hours, preferably 10 to 25 hours, at room temperature.

The formulations (padding liquor or printing paste) contain the quaternary ammonium salt of formula (1) in an appropriate concentration of 10 to 70 g per liter, preferably 25 to 50 g/l. In the case of the padding liquor, the pick-up is preferably 60 to 120% by weight.

In addition to the cationic reactive compound of formula (1), these formulations also include alkaline compounds such as potassium hydroxide or, preferably, sodium hydroxide. A 30% aqueous solution of sodium hydroxide is preferred, and is added to the formulation in a concentration of 20 to 50 ml/l, preferably 25 to 40 ml/l. The pH value of the preparations thus amounts as a rule to 8-13.5, preferably 10 to 12.

The formulations can also contain other conventional additives such as sodium chloride or sodium sulfate, urea, glycerin, thickening agents, e.g. alginates, ether starch or polyacylate, antioxidants, dispersing and wetting agents, homopolymers or copolymers of acrylamide or methacrylamide, or the graft polymers described in EP-A-111 454, as well as antifoams and other cationic fixing agents, which latter can also be fibre-reactive.

Suitable fibre material is regenerated or, particularly, natural cellulose, e.g. viscose staple, viscose rayon, hemp, linen, jute, or preferably cotton, as well as blends with synthetic fibres, e.g. of polyamide/cotton blends or, preferably, polyester/cotton blends.

The textiles can be used in any form, e.g. yarns, skeins of yarn, woven, knits, felts, preferably in the form of textile planar fabrics such as knit goods, fabrics and carpets, consisting wholly or partly of native, regenerated or modified cellulose.

Pretreatment of the cellulose material with the appropriate cationic compounds can be combined with other pretreatment processes. The relevant reactive fixing agent can, for example, be added to the alkaline bath in which raw cotton is usually boiled before dyeing to remove impurities. Thus cleaning and pretreatment with the fixing agent are performed in a single process.

Treatment of the cellulose fibre material is preferably carried out simultaneously with the dyeing. The dyeing is carried out with reactive or, preferably, with direct dyes by the cold pad batch in which the impregnation can be effected either by printing or by padding. The amount of dye is generally determined by the desired depth of colour and is conveniently 0.1 to 100 g/l of liquor, preferably 5 to 40 g/l.

If the cationic compound is used for pretreating the cellulosic fibre material, the dyeing can be produced by the exhaust process or by a two-stage process such as padding or printing. A suitable padding method is in particular the pad-steam, pad-fix or cold pad batch method.

Suitable substantive dyes are the customary direct dyes, for example those listed as "Direct Dyes" on pages 2005-2478 in volume 2 of the Colour Index (3rd edition, 1971).

By reactive dyestuffs are meant the customary dyes that form a chemical bond with the cellulose, e.g. those listed as "Reactive Dyes" on pages 3391-3560 in volume 3 (3rd edition, 1971) and on pages 6268-6345 in volume 6 (revised 3rd edition, 1975).

In the pretreatment with subsequent dyeing as well as in simultaneous application of the cationic fixing agent and dye, the process of this invention affords strong level dyeings which compared with those obtained by known dyeing procedures are distinguished by enhanced colour yield. In particular dyeings of substantially enhanced wetfastness are produced on cellulosic fibre material with substantive dyes.

In the following Preparatory and Application Examples, the percentages are by weight, unless otherwise stated. The amounts of dye refer to commercially available, i.e. standardised, product and the amounts of auxiliaries to pure substance. The five-figure Colour Index numbers (C.I.) refer to the 3rd edition of the Colour Index.

PREPARATORY EXAMPLES

EXAMPLE 1

72.5 g of dimethylaminopropylurea are dissoved in 49 g of water and to this solution is added at 20° C. a solution of 20 g of water and 49.3 g of 37% hydrochloric acid. The solution is heated to 60° C. Then 46.25 g epichlorhydrin is added dropwise over 30 minutes, whereupon the temperature rises to 72° C. After completion of the dropwise addition, the reaction mixture is stirred for 5 hours at 65° C.

Yields: 237 g of a solution of a compound of the formula:

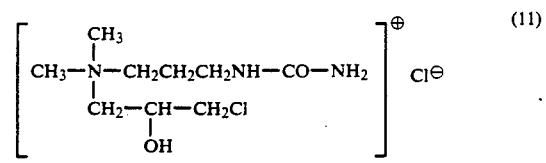

The epoxide and amine values are zero.
The pH value is 6.1.

EXAMPLE 2

89 g of dimethylaminoneopentylurea are dissolved in a solution of 86 g of water and 49.3 g of hydrochloric acid and heated to 60° C. Then 46.25 g of epichlorhydrin are added dropwise over 30 minutes, whereupon the temperature rises to 65° C. When the addition is complete, the solution is stirred for 5½ hours at 65° C. After this time the epoxide and amine values are zero. The yield consists of 270 g of a clear light yellow solution of a compound of formula

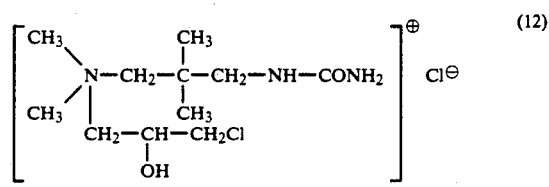

The pH value is 6.5.

EXAMPLE 3

76.0 g of [2-(1-pyrrolidinyl)ethyl]urea is dissolved in 55.4 g of water and to the solution is added at 20° C. a solution of 20 g of water and 49.3 g of 37% hydrochloric acid. The solution is heated to 60° C., then 46.25 g epichlorhydrin is added dropwise over 30 minutes, whereupon the temperature rises to 65° C. After the addition is complete, the solution is stirred for 4 hours at 65° C.

After this time the amine and epoxide values are zero. The yield consists of 247 g of a clear, light yellow solution of a compound of formula

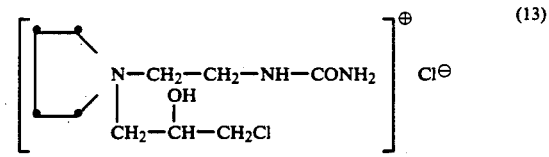

The pH value is 6.0.

EXAMPLE 4

83 g pf [3-(1-imidazolyl)propyl]urea are dissolved in 79.9 g water and to the solution is added at 20° C. a solution of 20 g of water and 49.3 g of 37% hydrochloric acid. The solution is then heated to 65° C. Then 46.25 g epichlorhydrin is added dropwise over 30 minutes, whereupon the temperature rises to 74° C. After the addition is complete, the solution is stirred for 2 hours at 70° C. After this time the amine number is 22 and the epoxide value is zero. The yield consists of 278.5 g of a clear yellow solution of a compound of formula:

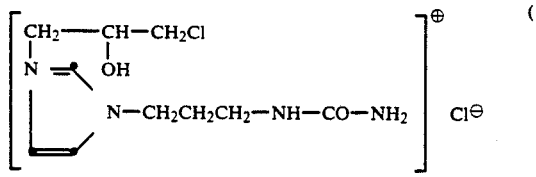

The pH value is 6.5.

EXAMPLE 5

94.5 g of [3-(1-morpholinyl)propyl]urea are dissolved in 94.5 g of water and to the solution is added a solution of 67.3 g of water and 49.3 g of hydrochloric acid. The solution is then heated to 60° C. Then 46.25 g epichlorhydrin are added dropwise over 30 minutes, whereupon the temperature rises to 64° C. After the addition is complete, the solution is stirred for 8 hours at 70° C. After this time the amine and epoxide values are zero. The yield consists of 350 g of a solution of a compound of formula:

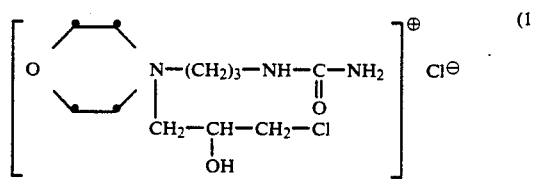

The pH value is 7.0.

EXAMPLE 6

86.2 g of [2-(1-piperidinyl)ethyl]urea are dissolved in 63.1 g of water and to the solution is added at 20° C. a solution of 20 g of water and 49.3 g of 37% hydrochloric acid. The solution is then heated to 60° C. Then 46.25 g epichlorhydrin are added dropwise over 30 minutes, whereupon the temperature rises to 67° C. After the addition is complete, the solution is stirred for 10 hours at 70° C.

After this time the amine and epoxide values are zero. The yield consists of 264 g of a solution of a compound of the formula

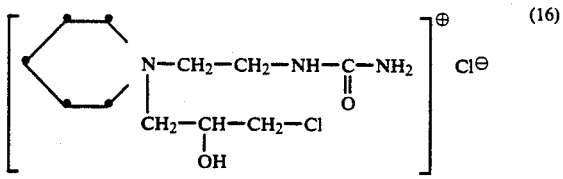

with a pH value of 7.5.

EXAMPLE 7

91.8 g of diethylaminopropylurea are dissolved in 68.7 g of water and to the solution is added at 20° C. a solution of 20 g of water and 49.3 g of 37% hydrochloric acid. The solution is heated to 60° C. 46.25 g of epichlorhydrin are then added dropwise over 30 minutes, whereupon the temperature rises to 65° C. After the addition is complete, the solution is stirred for 5 hours at 65° C. After this time the amine and epoxide values are zero. The yield consists of 275 g of a solution of a compound of formula:

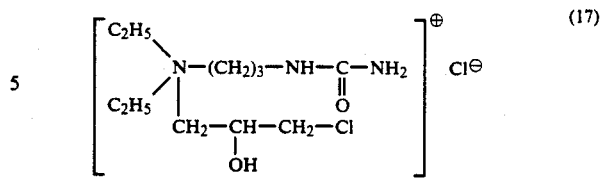

The pH value is 7.6.

EXAMPLE 8

70.5 g of dimethylaminopropylurea are dissolved in 71 g of water and to the solution is added at 10° C. a solution of 20 g of water and 25.5 g of 96% sulphuric acid. The solution is heated to 70° C. 46.25 g epichlorhydrin is then added over 30 minutes, whereupon the temperature rises to 80° C. After completion of the dropwise addition, the solution is stirred for 10 hours at 80° C. After this time the amine and epoxide values are zero. The yield consists of 232 g of a solution of a compound of following formula

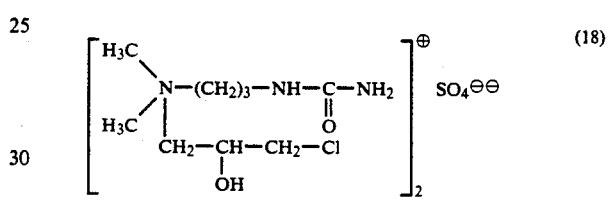

The pH value is 7.2.

EXAMPLE 9

77 g of N-(3-dimethylaminopropyl)-N'-methylolurea are dissolved in 54.3 g of water and to the solution is added a solution of 20 g of water and 43.4 g of 37% hydrochloric acid. The solution is heated to 45° C. Then 40.7 g epichlorhydrin are added dropwise over 30 minutes, whereupon the temperature rises to 50° C. After completion of the dropwise addition, the solution is stirred for 5 hours at 50° C. After this time the amine and epoxide values are zero. The yield consists of 235 g of a solution of a compound of formula:

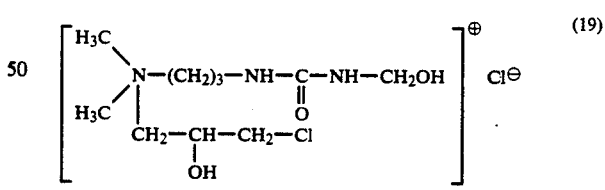

The pH value is 7.0.

APPLICATION EXAMPLES

EXAMPLE 1

20 g of cotton cretonne, bleached and unmercerised, are each impregnated on a padding mangle with one of the following 4 liquors, which each contain, per liter:

(1)

20 g of the dye Direct Red 80 C.I. 35780
32 ml of sodium hydroxide solution (30%)
35 g of the quaternary ammonium salt of formula (11)

(1)

25 g of a dye of formula

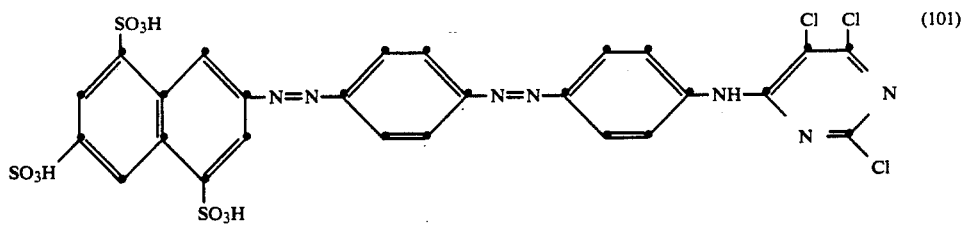

50 g of the quaternary ammonium salt of formula (11)
40 ml of sodium hydroxide solution (30%)
100 g of urea, and
3 g of the sodium salt of 3-nitrobenzenesulfonic acid.

(2)

25 g of a dye of formula:

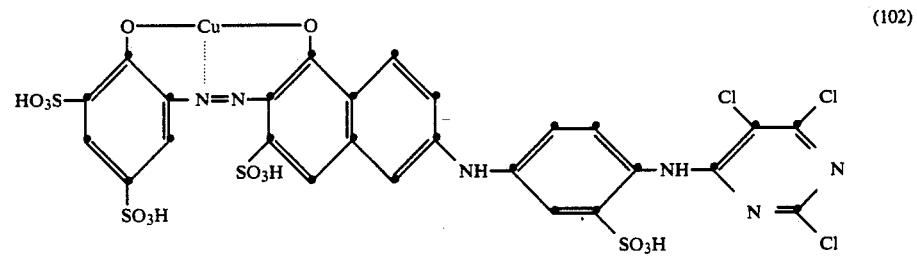

50 g of the quaternary ammonium salt of formula (11)
40 ml of sodium hydroxide solution (30%)
100 g of urea, and
3 g of the sodium salt of 3-nitrobenzenesulfonic acid.

(3)

25 g of a dye of formula:

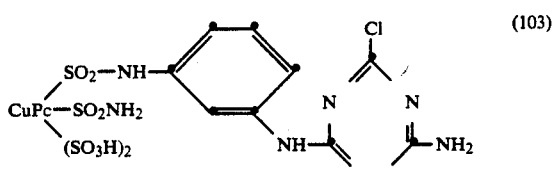

50 g of the quaternary ammonium salt of formula (11)
40 ml of sodium hydroxide solution (30%)
100 g of urea, and
3 g of the sodium salt of 3-nitrobenzenesulfonic acid.

(4)

25 g of a dye of formula:

(2)

12 g of the dye Direct Blue 71 C.I. 34140
32 ml of sodium hydroxide solution (30%)
35 g of the quaternary ammonium salt of formula (11)

(3)

12 g of the dye Direct Violet 77 C.I. 29125
32 ml of sodium hydroxide soluiton (30%)
35 g of the quaternary ammonium salt of formula (11)

(4)

20 g of the dye Direct Green 26 C.I. 34045
32 ml of sodium hydroxide solution (30%)
35 g of the quaternary ammonium salt of formula (11).

The liquor pick-up is in each case 80%. Thereafter the fabric is rolled up wet, packed airtight and stored for 18 hours at room temperature. The goods are then rinsed cold and hot and dried. The four dyeings are tested for the following fastness properties:
fastness to wet pressing (SN ISO 105-X11)
ISO C$_2$S-wash (ISO 105-C06)

Dyeings of comparable strength which have been obtained without addition of the quaternary ammonium salt of formula (11) are tested simultaneously.

The fastness ratings are listed in Table 1 below:

TABLE 1

| Dyeing | g/l Dye | Fastness to wet pressing | ISO C$_2$S-wash | |
|---|---|---|---|---|
| | | | Change of shade | Bleeding onto cotton |
| (1) without | 45 | 3–4 | 4 | 2 |
| with | 20 | 5 | 5 | 3–4 |
| (2) without | 16 | 2 | 4 | 2 |
| with | 12 | 5 | 5 | 5 |
| (3) without | 25 | 2–3 | 4–5 | 4 |
| with | 12 | 4–5 | 5 | 5 |
| (4) without | 35 | 4–5 | 4–5 | 3–4 |
| with | 20 | 5 | 5 | 5 |

EXAMPLE 2

20 g of cotton tricot, bleached and mercerised, are each impregnated on a padding mangle with one of the following 4 liquors, which each contain, per liter:

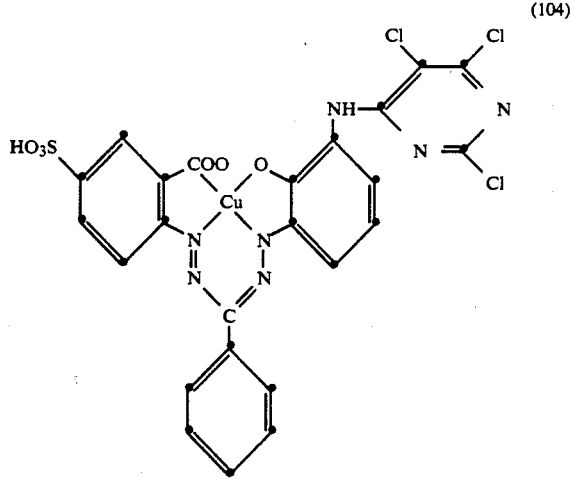

50 g of the quaternary ammonium salt of formula (11)
40 ml of sodium hydroxide (30%)
100 g of urea 3 g of the sodium salt of 3-nitrobenzenesulfonic acid.

The liquor pick-up in each case is 100%. Thereafter, the tricot pieces are rolled up wet and stored in airtight packing for 18 hours.

Then the goods are rinsed cold and hot and dried.

The four dyeings are tested for fastness to wet pressing and the ISO $C_2S$-wash. Dyeings of comparable strength, each containing more dye and which have been obtained without addition of the quaternary ammonium salt of formula (11), are also tested. The fastness ratings are compared in Table 2 below:

TABLE 2

| Dyeing | | g/l Dye | Fastness to wet pressing | ISO $C_2S$-wash Change of shade | Bleeding onto cotton |
|---|---|---|---|---|---|
| (1) | without | 40 | 4–5 | 5 | 4–5 |
|  | with | 25 | 5 | 5 | 4–5 |
| (2) | without | 37 | 4 | 5 | 4–5 |
|  | with | 25 | 5 | 5 | 4–5 |
| (3) | without | 35 | 4–5 | 5 | 4 |
|  | with | 25 | 5 | 5 | 5 |
| (4) | without | 38 | 4–5 | 5 | 5 |
|  | with | 25 | 5 | 5 | 5 |

Comparably good effects are obtained by using 50 g/l of each of the quaternary ammonium salts produced in accordance with Examples 2 to 4.

EXAMPLE 3

20 g of cotton tricot, bleached and mercerised are each padded to a liquor pick-up of 90% with a formulation containing, per liter:

35 g of the quaternary ammonium salt of formula (11)
30 ml of sodium hydroxide solution (30%).

After padding, the tricot is rolled up wet and stored in a plastic sack for 18 hours at room temperature. Then the goods are rinsed hot and cold.

The pretreated tricot, together with 20 g of non-treated tricot, is impregnated at 50° C. with an aqueous dye liquor which, at a liquor ratio of 1:40, contains 1% of the dye Direct Blue 71 C.I. 43140. The temperature is raised to 98° C. over 30 minutes, and dyeing is carried out for 45 minutes at this temperature. Of the two tricot pieces, the pretreated piece is dyed dark blue, whereas the non-pretreated material is only lightly dyed.

EXAMPLE 4

The tricot pretreated according to Example 3, together with 20 g non-pretreated tricot, is impregnated at 98° C. with an aqueous liquor which contains, at a liquor ratio of 1:30, 1% of the dye of formula:

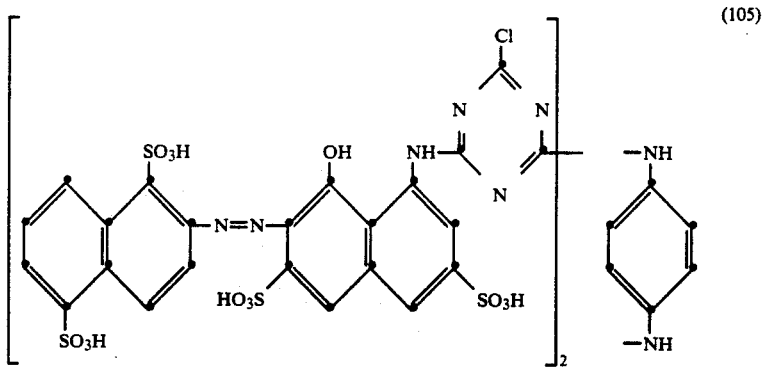

The temperature is then lowered to 85° C. over 30 minutes,
5 g/l of calcined sodium carbonate
2 ml/l of sodium hydroxide solution (30%)
are then added and the material is treated for a further 45 minutes at 85° C. The dyeings are then rinsed for 5 minutes in boiling water.

Of the two pieces of tricot, the pretreated tricot is dyed deep red, whereas the non-pretreated material is only dyed light pink.

EXAMPLE 5

The tricot pretreated according to Example 3, together with 20 g of non-pretreated tricot and 20 g of tricot treated in the same manner but only with 30 ml/l of sodium hydroxide solution (30%), is impregnated at 50° C. with an aqueous liquor which, at a liquor ratio of 1:40, contains 1% of a dye of formula

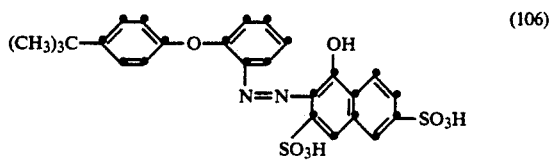

The material is then dyed for 40 minutes at 50° C. and thereafter rinsed warm for 5 minutes.

Of the three pieces of tricot, the tricot pretreated in accordance with Example 3 is dyed deep red, whereas the 2 other tricot pieces are only lightly dyed.

EXAMPLE 6

20 g cotton tricot, bleached and mercerised, are each impregnated on a padding mangle with one of the 4 following liquors which contain, per liter:

(1)

18 g of the dye of formula

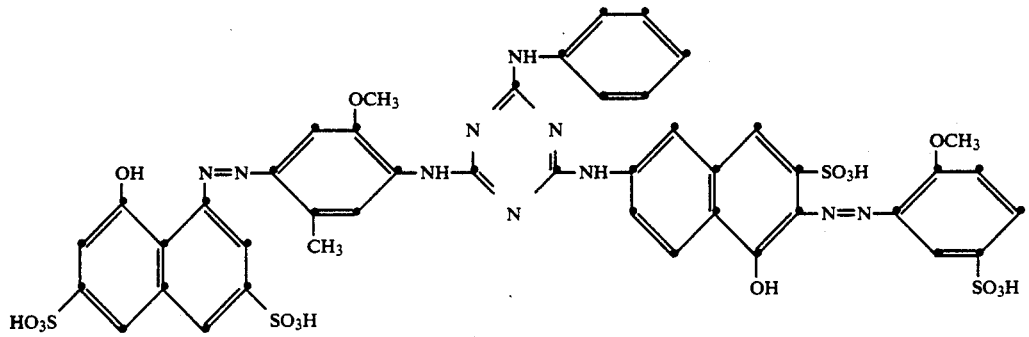

(107)

32 ml of sodium hydroxide solution (30%) of
35 g of the quaternary ammonium salt of formula (19).

(2)

18 g of the dye Direct Red 80 C.I. 35780
32 ml of sodium hydroxide 30%
35 g of the quaternary ammonium salt of formula (19).

(3)

8 g of the dye Direct Blue 71 C.I. 34240
32 ml of sodium hydroxide solution (30%)
35 g of the quaternary ammonium salt of formula (19).

(4)

8 g of the dye of formula

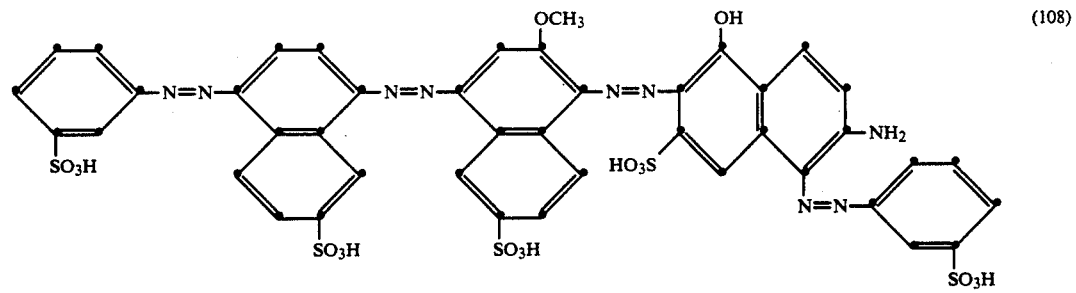

(108)

32 ml of sodium hydroxide solution (30%)
35 g of the quaternary ammonium salt of formula (19).

The liquor pick-up is 90% in each case. The pieces of tricot are then rolled up wet, packed airtight and stored for 18 hours at room temperature. The goods are then rinsed cold and hot and dried.

EXAMPLE 7

The procedure of Application Example 6 is repeated, replacing the quaternary ammonium salt of formula (19) by respectively 1. 35 g/l of the quaternary ammonium salt of formula (18)
2. 35 g/l of the quaternary ammonium salt of formula (15)
3. 35 g/l of the quaternary ammonium salt of formula (16)
4. 35 g/l of the quaternary ammonium salt of formula (17).

The 20 dyeings obtained in Applications Examples 6 and 7 are tested for the following fastness properties:
fastness to wet pressing
ISI $C_2S$-wash.

Dyeings of corresponding strength obtained without addition of the quaternary ammonium salts were also tested. The fastness ratings are listed in Table 3 below.

TABLE 3

| Dyeing | g/l Dye for dyeing of equal intensity | Fastness to wet pressing | ISO $C_2S$-wash Change of shade | Bleeding onto cotton |
|---|---|---|---|---|
| (1) without | 25 | 3 | 4 | 2-3 |
| formula (19) | 18 | 5 | 4-5 | 4 |
| formula (18) | 18 | 5 | 4-5 | 4 |
| formula (15) | 18 | 5 | 4-5 | 3-4 |
| formula (16) | 18 | 5 | 5 | 4 |
| formula (17) | 18 | 5 | 4-5 | 4 |
| (2) without | 38 | 3 | 4 | 2 |
| formula (19) | 18 | 5 | 4-5 | 4 |
| formula (18) | 18 | 5 | 4-5 | 4 |
| formula (15) | 18 | 5 | 4-5 | 3-4 |
| formula (16) | 18 | 5 | 4-5 | 3-4 |
| formula (17) | 18 | 5 | 5 | 4 |
| (3) without | 14 | 2 | 4 | 2 |
| formula (19) | 8 | 5 | 4-5 | 4-5 |
| formula (18) | 8 | 5 | 4-5 | 4-5 |
| formula (15) | 8 | 5 | 4-5 | 4 |
| formula (16) | 8 | 5 | 4-5 | 3-4 |
| formula (17) | 8 | 5 | 5 | 4 |
| (4) without | 16 | 3 | 4-5 | 3-4 |
| formula (19) | 8 | 5 | 5 | 5 |
| formula (18) | 8 | 5 | 5 | 5 |
| formula (15) | 8 | 5 | 5 | 4-5 |

TABLE 3-continued

| Dyeing | g/l Dye for dyeing of equal intensity | Fastness to wet pressing | ISO C₂S-wash Change of shade | ISO C₂S-wash Bleeding onto cotton |
|---|---|---|---|---|
| formula (16) | 8 | 5 | 5 | 5 |
| formula (17) | 8 | 5 | 5 | 4-5 |

What is claimed is:

1. A process for enhancing the colour yield and the wet-fastness of dyeings or printings obtained with anionic dyes on cellulosic fibre material, which comprises treating the fibre material before or during dyeing with a quaternary ammonium salt, which is obtainable by reaction of a basic carbamide containing a quaternisable nitrogen atom with an epihalohydrin, said quaternary ammonium salt having the formula

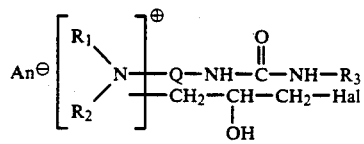  (1)

wherein

Q represents alkylene of 2 to 6 carbon atoms $R_1$ and $R_2$ are each independently of the other, lower alkyl unsubstituted or substituted by halogen, hydroxyl, cyano or lower alkoxy, or cycloalkyl or aralkyl, or $R_1$ and $R_2$ together with the nitrogen atom to which they are attached are a five- or six-membered heterocyclic radical, which optionally contains an additional heteroatom $R_3$ is a hydrogen, lower alkyl or hydroxy-lower alkyl, Hal is halogen and An⊖ is the anion of an inorganic or organic acid and the

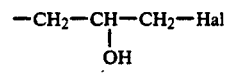

group in formula (1) is bound to a quaternary nitrogen atom.

2. A process according to claim 1, wherein the treatment is carried out semicontinuously by the cold pad-batch method.

3. A process according to claim 2, wherein the treatment is carried out by the cold pad-batch method and during dyeing.

4. A process according to claim 1, wherein the treatment is carried out in alkaline medium.

5. A process according to claim 1, wherein the treatment is carried out by using the cellulosic material dyed with substantive dyes.

* * * * *